(12) United States Patent
Klein

(10) Patent No.: US 10,131,610 B2
(45) Date of Patent: Nov. 20, 2018

(54) METHODS OF PRODUCING DICARBONYL COMPOUNDS

(71) Applicant: EMPIRE TECHNOLOGY DEVELOPMENT LLC, Wilmington, DE (US)

(72) Inventor: Josef Peter Klein, Vashon, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 15/032,045

(22) PCT Filed: Oct. 25, 2013

(86) PCT No.: PCT/US2013/066827
§ 371 (c)(1),
(2) Date: Apr. 25, 2016

(87) PCT Pub. No.: WO2015/060862
PCT Pub. Date: Apr. 30, 2015

(65) Prior Publication Data
US 2016/0257638 A1  Sep. 8, 2016

(51) Int. Cl.
| | | |
|---|---|---|
| C07C 69/34 | (2006.01) | |
| C07C 51/36 | (2006.01) | |
| C07C 29/42 | (2006.01) | |
| C07C 67/08 | (2006.01) | |
| C07C 67/303 | (2006.01) | |
| C07C 51/15 | (2006.01) | |
| C07C 1/30 | (2006.01) | |
| C07C 17/16 | (2006.01) | |
| C10B 53/02 | (2006.01) | |
| C07C 21/22 | (2006.01) | |

(52) U.S. Cl.
CPC .............. *C07C 51/36* (2013.01); *C07C 1/30* (2013.01); *C07C 17/16* (2013.01); *C07C 21/22* (2013.01); *C07C 29/42* (2013.01); *C07C 51/15* (2013.01); *C07C 67/08* (2013.01); *C07C 67/303* (2013.01); *C10B 53/02* (2013.01); *Y02E 50/14* (2013.01)

(58) Field of Classification Search
None
See application file for complete search history.

(56) References Cited

U.S. PATENT DOCUMENTS

| | | |
|---|---|---|
| 3,853,961 A | 12/1974 | Birkenstock et al. |
| 4,681,707 A | 7/1987 | Alper et al. |
| 5,179,175 A | 1/1993 | Speranza et al. |
| 5,260,246 A | 11/1993 | Yuo et al. |
| 5,264,541 A | 11/1993 | Yuo et al. |
| 5,346,984 A | 9/1994 | Hasegawa et al. |
| 5,468,900 A | 11/1995 | Moran, Jr. et al. |
| 6,011,134 A | 1/2000 | Marks et al. |
| 6,040,392 A | 3/2000 | Khanna et al. |
| 6,075,117 A | 6/2000 | Hayes et al. |
| 6,331,624 B1 | 12/2001 | Koch et al. |
| 6,362,307 B1 | 3/2002 | Mohrschlad et al. |
| 6,437,089 B1 | 8/2002 | Cohen et al. |
| 6,472,501 B1 | 10/2002 | Fergusson et al. |
| 6,699,960 B1 | 3/2004 | Ohlbach et al. |
| 6,835,800 B2 | 12/2004 | Way et al. |
| 7,060,678 B2 | 6/2006 | Prasad et al. |
| 7,977,450 B2 | 7/2011 | Frost |
| 8,501,989 B2 | 8/2013 | Boussie et al. |
| 8,558,018 B2 | 10/2013 | Sanborn |
| 8,735,530 B2 | 5/2014 | Thieblemont et al. |
| 8,859,816 B2 | 10/2014 | Lomel |
| 9,150,691 B2 | 10/2015 | Jeol |
| 9,637,595 B2 | 5/2017 | Jeol et al. |
| 2002/0183478 A1 | 12/2002 | Fergusson et al. |
| 2003/0130478 A1 | 7/2003 | Way et al. |
| 2003/0135018 A1 | 7/2003 | Way et al. |
| 2004/0022677 A1 | 2/2004 | Wohlstadter et al. |
| 2004/0214982 A1 | 10/2004 | Alsop et al. |
| 2008/0132636 A1 | 6/2008 | Ross et al. |
| 2009/0137385 A1 | 5/2009 | Park et al. |
| 2010/0152481 A1 | 6/2010 | Staffel et al. |
| 2010/0317822 A1 | 12/2010 | Boussie et al. |
| 2011/0190442 A1 | 8/2011 | Buzinkai et al. |
| 2012/0077252 A1 | 3/2012 | Picataggio et al. |
| 2012/0122240 A1 | 5/2012 | Geddes |
| 2012/0199298 A1 | 8/2012 | Dyer |
| 2013/0095272 A1 | 4/2013 | Carman, Jr. et al. |

FOREIGN PATENT DOCUMENTS

| | | |
|---|---|---|
| CN | 101679194 A | 5/2010 |
| CN | 102356113 A | 2/2012 |
| CN | 102459214 A | 5/2012 |
| CN | 102803196 A | 11/2012 |

(Continued)

OTHER PUBLICATIONS

Nozoe et al. Solid State Ionics (2001, vol. 141-142, p. 695-700.*
Verkruijsse et al. Organometallics 2004, 23, 4382-4390.*
Johnson, J. Chem. Soc. 1946, 1009-1014.*
Amarasekara et al., Efficient oxidation of 5-hydroxymethylfurfural to 2,5-diformylfuran using Mn(III)—salen catalysts, Catalysis Communications(2008), (9) pp. 286-288.
Aoyama and Novak, Another Synthesis Route to New Materials: Hydrogenation of Heteroaromatic Polymers, accessed at http://www.iiis.org/cds2008/cd2008sci/SCI2008/PapersPdf/S464BA.pdf, accessed on Apr. 29, 2016, pp. 1-3.

(Continued)

*Primary Examiner* — Ana Z Muresan

(57) ABSTRACT

Dicarboxylic acids, such as adipic acid, and diesters, such as adipates, may be produced by hydrogenating alkynes that may be produced from raw materials salvaged from waste stream processes. The carbons of the dicarboxylic acids are provided by alkynes generated from biomass waste and carbon dioxide recovered from waste streams such as exhaust gases.

10 Claims, 3 Drawing Sheets

(56) References Cited

FOREIGN PATENT DOCUMENTS

| | | | |
|---|---|---|---|
| CN | 103025794 A | 4/2013 | |
| CN | 104937010 A | 9/2015 | |
| EP | 2941447 A1 | 11/2015 | |
| GB | 924422 A | 4/1963 | |
| WO | 2002098954 A1 | 12/2002 | |
| WO | 2009066975 A1 | 5/2009 | |
| WO | 2010105939 A1 | 9/2010 | |
| WO | 2010132740 A3 | 11/2010 | |
| WO | 2010144873 A1 | 12/2010 | |
| WO | 2011095684 A1 | 8/2011 | |
| WO | 2011149339 A1 | 12/2011 | |
| WO | 2012013481 A1 | 2/2012 | |
| WO | WO 2012022801 | * | 2/2012 |
| WO | 2013007585 A1 | 1/2013 | |
| WO | 2013109447 A1 | 7/2013 | |
| WO | 2014106485 A1 | 7/2014 | |

OTHER PUBLICATIONS

Aoyama and Novak, Pyridine Rings as Protected 2° Amines: Facile Hydrogenation of Heterocyclic Aromatic Polymers, Macromolecules (2001), (34) pp. 6842-6844.

Block et al., Perthio- and perseleno-1,3-butadienes, -but-1-ene-3-ynes, and —[3]-cumulenes: One-step synthesis from 1,4-dilithio-1,3-butadiynes, Organic Letters (Mar. 27, 2003), 5(8) pp. 1325-1327.

Boustead, Eco-profiles of the European Plastics Industry: Polyamide 6 (Nylon 6), PlasticsEurope (Mar. 2005), pp. 1-15.

Brasholz et al., Highly efficient dehydration of carbohydrates to 5-(chloromethyl)furfural (CMF), 5-(hydroxymethyl) furfural (HMF) and levulinic acid by biphasic continuous flow processing, Green Chemistry (2011), 13(5) pp. 1114-1117.

Buntara et al., Caprolactam from Renewable Resources: Catalytic Conversion of 5-Hydroxymethylfurfural into Caprolactone, Angewandte Chemie International Edition (Jul. 25, 2011), 50(31) pp. 7083-7087.

Chakraborty et al., Cyclic trimer of 5-(aminomethyl)-2-furancarboxylic acid as a novel synthetic receptor for carboxylate recognition, Tetrahedron Letters (Feb. 11, 2002), 43(7) pp. 1317-1320.

Chang et al., The ethynylation of formaldehyde in a three-phase slurry reactor, Chemical Engineering Science (Sep.-Oct. 1992), 47(13-14) pp. 3793-3800.

Chu et al., Kinetics of the synthesis of 1,4-butynediol over copper-bismuth/magnesium silicate catalyst, Applied Catalysis A: General (Apr. 23, 1993), 97(2) pp. 123-132.

Dangerfield et al., Protecting-Group-Free Synthesis of Amines: Synthesis of Primary Amines from Aldehydes via Reductive Amination, Journal of Organic Chemistry (Jul. 28, 2010), 75(16) pp. 5470-5477.

Gehlsen and Bates, Heterogeneous Catalytic Hydrogenation of Poly(styrene): Thermodynamics of Poly (vinylcyclohexane) Containing Diblock Copolymers, Macromolecules (1993), (26) 4122-4127.

Georgieff and Richard, Diacetylene: Preparation, Purification, and Ultraviolet Spectrum, Canadian Journal of Chemistry (Sep. 1958), 36(9) pp. 1280-1283.

Herzog and Smiley, Hexamethylenediamine, Ullmann's Encyclopedia of Industrial Chemistry (2011), pp. 1-5.

Homsi and Rousseau, Halodecarboxylation of α,β-acetylenic and α,β-ethylenic acids, Tetrahedron Letters (Feb. 19, 1999), 40(8) pp. 1495-1498.

International Search Report and Written Opinion for International Application No. PCT/US2013/066171 dated Feb. 21, 2014.

International Search Report and Written Opinion for International Application No. PCT/US2013/066136 dated Feb. 24, 2014.

International Search Report and Written Opinion for International Application No. PCT/US2013/066827 dated Mar. 3, 2014.

Izumi, Recent advances in the photocatalytic conversion of carbon dioxide to fuels with water and/or hydrogen using solar energy and beyond, Coordination Chemistry Reviews (Jan. 2013), 257(1) pp. 171-186.

Janka et al., Synthesis of Neutral Molecular Squares Composed of Bis(phosphine)platinum Corner Units and Dialkynyl Linkers. Solid-State Characterization of [Pt(μ-C i CC i C)(dppp)]4,Organometallics (Aug. 18, 2004), 23(19) pp. 4382-4390.

Kohan et al., Polyamides, Ullmann's Encyclopedia of Industrial Chemistry (2012), (28) pp. 537-572.

Lapina et al., Reactions of alkyl (halomethyl)furancarboxylates with hexamethylenetetramine, Russian Journal of Genereal Chemistry (Aug. 2006), 76(8) pp. 1304-1309.

Lewkowski, Synthesis, chemistry and applications of 5-hydroxymethylfurfural and its derivatives, ARKIVO (2001), 2001(1) pp. 17-54.

Lichtenthaler, Carbohydrates as organic raw materials, Ullmann's Encyclopedia of Industrial Chemistry (2012), (6) pp. 583-616.

Manjolinho et al., Catalytic C-H carboxylation of terminal alkynes with carbon dioxide, American Chemical Society Catalysis (Aug. 13, 2012), 2(9) pp. 2014-2021.

Mares and Sheehan, Kinetics of Caprolactam Formation From 6-Aminocaproic Acid, Ester, and Amide, Industrial & Engineering Chemistry Process Design and Development (Jan. 1978), 17(1) pp. 9-16.

Maretina and Trofimov, Diacetylene: a candidate for industrially important reactions, Russian Chemical Reviews (Jul. 2000), 69(7) pp. 591-608.

Mascal and Nikitin, Direct, high-yield conversion of cellulose into biofuel, Angew Chem Int Ed Engl. (2008), 47(41) pp. 7924-7926.

Mascal and Nikitin, Dramatic advancements in the saccharide to 5-(chloromethyl)furfural conversion reaction, ChemSusChem (2009), 2(9) pp. 859-861.

Mascal and Nikitin, Towards the efficient, total glycan utilization of biomass, ChemSusChem (2009), 2(5) pp. 423-426.

Mei et al., TEMPO-Mediated Oxidation of Primary Alcohols to Carboxylic Acids by Exploitation of Ethers in an Aqueous—Organic Biphase System, Bulletin of the Chemical Society of Japan (2009), 82(8) pp. 1000-1002.

Mitiakoudis and Gandini, Synthesis and characterization of furanic polyamides, Macromolecules (Feb. 1991), 24(4) pp. 830-835.

Musser, Adipic Acid, Ullmann's Encyclopedia of Industrial Chemistry (2005), pp. 1-11.

Passler et al., Acetylene, Ullmann's Encyclopedia of Industrial Chemistry (2012), (1) pp. 277-326.

Ritz et al., Caprolactam, Ullmann's Encyclopedia of Industrial Chemistry (2012), pp. 1-20.

Sakurai et al., DNA-Templated Functional Group Transformations Enable Sequence-Programmed Synthesis Using Small-Molecule Reagents, Journal of American Chemical Society (Jan. 22, 2005), 127(6) pp. 1660-1661.

Stang and Learned, Generation and trapping of an alkatrienylidenecarbene, Journal of the Chemical Society, Chemical Communications (1988), (4) pp. 301-302.

Tashiro et al., Reduction of Unsaturated Aliphatic Mono- and Dicarboxylic Acids and Brominated Aliphatic Acids with Raney Alloys in an Alkaline Solution, Affording the Corresponding Saturated Aliphatic Acids, Rep. Inst. Advanced Material Study (Dec. 1988), 2(2) pp. 261-268.

Van Swieten et al., Development of an isotope-coaded activity-based probe for the quantitative profiling of cysteine proteases, Bioorganic & Medicinal Chemistry Letters (Jun. 21, 2004), 14(12) pp. 3131-3134.

Yang et al., Conversion of biomass into 5-hydroxymethylfurfural using solid acid catalyst, Bioresource Technology (Feb. 2011), 102(3) pp. 3424-3429.

Zakrzewska et al., Ionic Liquid-Mediated Formation of 5-Hydroxymethylfurfural—A Promising Biomass-Derived Building Block, Chemical Reviews (Oct. 25, 2010), 111(2) pp. 397-417.

Zhang et al., Selective Oxidation of Benzylic Alcohols and TBDMS Ethers to Carbonyl Compounds with CrO3-H5IO6, Synthesis (2005), (11) pp. 1757-1760.

Extended European Search Report for counterpart Patent Application No. 13895980.4 dated May 17, 2017, pp. 8.

Extended European Search Report for counterpart Patent Application No. 13896041.4 dated May 16, 2017, pp. 11.

(56) References Cited

OTHER PUBLICATIONS

Walker, D.P., et al., "Synthesis of (±)-8-0xa-3-azabicyclo[3.2.I]octan-2-thione and (±)-2-0xa-5-azabicyclo[2.2.I] heptan-6-thione: Potential Synthons for the Preparation of Novel Heteroaryl-Annulated Bicyclic Morpholines," Synthesis, vol. 2011, No. 7, pp. 1113-1119 (Mar. 8, 2011).
Zhao, M., et al., "A Novel Chromium Trioxide Catalyzed Oxidation of Primary Alcohols to Carboxylic Acids," Tetrahedron Letters, vol. 39, Issue 30, pp. 5323-5326 (Jul. 23, 1998).
The Size of the Global in Vitro Diagnostic Market Was in Excess of US$ 38 Billion, accessed at http://www.reuters.com/article/idUS107243+27-May-2008+BW20080527, posted on May 27, 2008, pp. 3.
Almeida et al., Guiding and confining light in void nanostructure, Optics Letters (Jun. 1, 2004), 29(11) pp. 1209-1211.
Anker et al., Biosensing with plasmonic nanosensors, Nature Materials (Jun. 2008), (7) pp. 442-453.
Aslan et al., Plasmon light scattering in biology and medicine: new sensing approaches, visions and perspectives, Current Opinion in Chemical Biology (Oct. 2005), 9(5) pp. 538-544.
Barnett et al., Coupled plasmon effects for the enhancement of fluorescent immunoassays, Physica B: Condensed Matter (May 15, 2007), 394(2) pp. 297-300.
Chen et al., Plasmon-Enhanced Colorimetric ELISA with Single Molecule Sensitivity, Nano Lett. (Mar. 23, 2011), 11(4) pp. 1826-1830.
Cho and Park, Serodiagnostic comparison between two methods, ELISA and surface plasmon resonance for the detection of antibodies of classical swine fever, Journal of Vet. Med. Sci. (Dec. 2006), 68(12) pp. 1327-1329.
Ha et al., Single-molecule fluorescence spectroscopy of enzyme conformational dynamics and cleavage mechanism, Proc. Natl. Acad. Sci. USA (Feb. 1999), 96(3) pp. 893-898.
Han et al., Surface-enhanced Raman scattering for protein detection, Anal. Bioanal. Chem. (Aug. 2009), 394(7) pp. 1719-1727.
Hao and Schatz, Electromagnetic fields around silver nanoparticles and dimmers, Journal of Chemical Physics (Jan. 1, 2004), 120(1) pp. 357-366.
Homola, Surface Plasmon Resonance Sensors for Detection of Chemical and Biological Species, Chem. Rev. (Jan. 30, 2008), 108(2) pp. 462-493.
International Search Report and Written Opinion for International Application No. PCT/US13/62633, dated Apr. 15, 2014.
Jain et al., Plasmon Coupling in Nanorod Assemblies: Optical Absorption, Discrete Dipole Approximation Simulation, and Exciton-Coupling Model, J. Phys. Chem. B (Aug. 30, 2006), 110(37) pp. 18243-18253.
Lakowicz, Plasmonics in Biology and Plasmon-Controlled Fluorescence, Plasmonics (Mar. 1, 2006), 1(1) pp. 1-70.
Lakowicz et al., Plasmon-controlled fluorescence: a new paradigm in fluorescence spectroscopy, Analyst. (Jul. 16, 2008), 133(10) pp. 1-109.
Li et al., Mass Synthesis of Large, Single-Crystal Au Nanosheets Based on a Polyol Process, Adv. Funct. Mater. (Jan. 2006), 16(1) pp. 83-90.
Lofgren et al., Comparing ELISA and Surface Plasmon Resonance for Assessing Clinical Immunogenicity of Panitumumab, J. of Immun. (Jun. 1, 2007), 178(11) pp. 7467-7472.
Martelli et al., Self-assembled porphyrin microrods and observation of structure-induced iridescence, Journal of Materials Chemistry (Jan. 2010), 20(12) pp. 2310-2316.
Matveeva et al., Metal-enhanced fluorescence immunoassays using total internal reflection and silver island-coated surfaces, Analytical Biochemistry (Nov. 15, 2004), 334(2) pp. 303-311.
McFarland et al., Wavelength-Scanned Surface-Enhanced Raman Excitation Spectroscopy, J. Phys. Chem. B (May 14, 2005), 109(22) pp. 11279-11285.

Muhlschlegel et al., Resonant Optical Antennas, Science (Jun. 10, 2005), 308(5728) pp. 1607-1609.
Nooney et al., Enhancing the analytical performance of immunoassays that employ metal-enhanced fluorescence, Anal Bioanal Chem. (Feb. 2010), 396(3) pp. 1127-1134.
Rica and Stevens, Plasmonic ELISA for the ultrasensitive detection of disease biomarkers with the naked eye, Nature Nanotechnology (Oct. 28, 2012), 7(821-824).
Schmitt et al., Interferometric biosensor based on planar optical waveguide sensor chips for label-free detection of surface bound bioreactions, Biosensors Bioelectronics (May 15, 2007), 22(11) pp. 2591-2597.
Sorensen et al., Enhanced fluorescence emission of Me-ADOTA+ by self-assembled silver nanoparticles on a gold film, Chemical Physics Letters (Jul. 7, 2009), 476(1-3) pp. 1-12.
Stuart et al., Biological applications of localised surface plasmonic phenomenae, IEE Proc. Nanobiotechnol. (Feb. 2005), 152(1) pp. 13-32.
Tabor et al., On the Use of Plasmonic Nanoparticle Pairs as a Plasmon Ruler: The Dependence of the Near-Field Dipole Plasmon Coupling on Nanoparticle Size and Shape, J. Phys. Chem. A (Mar. 2009), 113(10) pp. 1946-1953.
Wallrabe and Periasamy, Imaging protein molecules using FRET and FLIM microscopy, Current Opinion in Biotechnology (Feb. 2005), 16(1) pp. 19-27.
Wu et al., Double-antigen sandwich time-resolved immunofluorometric assay for the detection of anti-hepatitis C virus total antibodies with improved specificity and sensitivity, Journal of Medical Microbiology (2008), 57(8) pp. 947-953.
Yang et al., Discrete dipole approximation for calculating extinction and Raman intensities for small particles with arbitrary shapes, J. of Chem. Phys. (Jul. 15, 1995), 103(3) pp. 869-875.
Zhou et al., Enhancement of Immunoassay's Fluorescence and Detection Sensitivity Using Three-Dimensional Plasmonic Nano-Antenna-Dots Array, Anal. Chem. (Apr. 20, 2012), 84(10) pp. 4489-4495.
Zolotavin et al., Two-photon luminescence enhancement of silver nanoclusters photodeposited onto mesoporous $TiO_2$ film, Chemical Physics Letters (May 2008), 457(4-6) pp. 342-346.
Burlison and Blagg, "Syntesis and Evaluation of Coumermycin A1 Analogues that Inhibit the Hsp90 Protein Folding Machinery" Organic Letters (Sep. 20, 2006), 8(21) pp. 4855-4858.
Yu and Zhang, "Copper- and copper-N-heterocyclic carbene-catalyzed C-H activating carboxylation of terminal alkynes with $CO_2$ at ambient conditions" PNAS (Nov. 23, 2010), 107(47) pp. 20184-20189.
Xing et al., "Preparation method of haloalkane, preparation method of alkyne, reaction of alkyne, preparation method of carboxylic acid" Basic Organic Chemistry, Higher Education Press (Nov. 30, 1993), pp. 153, 218-220, 222-223, 539.
Lin et al., "Acetylene synthesis method of butyl alkyne aldehyde glycol catalyst" Petrochemical Engineering (Dec. 31, 1987), 16(5) pp. 265-269.
Ren, "Methods of producing formaldehyde with $CO_2$ catalytic hydrogenation" Formaldehyde and Methanol (Dec. 31, 2002), (3) pp. 13-15.
Graef et al., "Product Distribution in the Rapid Pyrolysis of Biomass/Lignin for Production of Acetylene", Biomass as a Nonfossil Fuel Source (Mar. 24, 2010), (15) pp. 293-312.
Moreau et al., Recent catalytic advances in the chemistry of substituted furans from carbohydrates and in the ensuing polymers, Topics in Catalysis (Feb. 2004), 27(1-4) pp. 11-30.
Moore et al., "Ion-Binding Polyesters and Polyamides Containing THF Rings," in the Crown Ethers and Phase Transfer Catalysis in Polymer Science, pp. 291-327, Mathihas, L. and Carraher, C.E, eds., Polymer Science and Technology (Sep. 1984).

\* cited by examiner

METHODS OF PRODUCING DICARBONYL COMPOUNDS

CROSS-REFERENCE TO RELATED APPLICATIONS

This application is a U.S. national stage filing under 35 U.S.C. § 371 of International Application No. PCT/US2013/066827 filed on Oct. 25, 2013 entitled "METHODS FOR PRODUCING DICARBONYL COMPOUNDS," which is incorporated herein by reference in its entirety.

BACKGROUND

Dicarbonyl compounds may include dicarboxylic acids, organic compounds that contain two carboxylic acid (—COOH) functional groups, and diesters, organic compounds that contain two ester functionalities (—COOR, where R may be an alkyl group or other organic moiety). Dicarbonyl compounds may be straight chain, branched chain, or aromatic, and are suitable substrates for preparing organic constituents for the pharmaceutical and food industries. For example, dicarboxylic acids are useful materials for preparing fragrances, polyamides, adhesives, lubricants, polyesters, and other commercially valuable products.

Adipic acid, as an example dicarboxylic acid, is a commodity chemical with global production on the order of 2.5 million metric tons, annually, and the primary commercial use of adipic acid is as a monomer in the manufacture of Nylon 6,6. Nylon 6,6 is a polyamide of the diamine hexamethylenediamine (IUPAC name: hexane-1,6-diamine) and the dicarboxylic acid adipic acid (IUPAC name: hexanedioic acid) and may be produced by the polycondensation of the diamine and the dicarboxylic acid. Types of nylons, such as Nylon 6,6, are distinguished by a numerical suffix that specifies the numbers of carbons donated by the monomers, with the number of carbons from the diamine monomer listed first, followed by the number of carbons from the dicarboxylic acid monomer. Other nylons that may be formed from dicarboxylic acids may include Nylon 6,9, Nylon 6,12, and Nylon 4,6.

Adipic acid and esters thereof (adipates), as well as other dicarboxylic acids and diesters, are often produced from the petrochemically derived raw materials benzene or butadiene. Efforts to replace these petrochemically derived raw materials are ongoing, and there remains a need to provide alternative scalable and cost effective approaches for commercially producing diesters and dicarboxylic acids using alternative carbon sources.

SUMMARY

Trapping of carbon dioxide from waste emissions and incorporation of the carbon dioxide into commodity chemicals that may be useable in producing diesters, dicarboxylic acids, or other materials, provides an alternative method for producing diesters and dicarboxylic acids while reducing waste carbon dioxide emissions into the atmosphere. In some embodiments, the methods disclosed herein use waste carbon dioxide streams.

In an embodiment, a method for producing dicarbonyl compounds of formula I: ROOC—$(CH_2)_n$—COOR, wherein R is —H, alkyl, or substituted alkyl, and n≥2, includes hydrogenating a bis-carbonyl alkyne of formula II: ROOC—$(C_nH_{2n-4m})$—COOR, wherein m is a number of (—C≡C—) and $n/2 \geq m \geq 1$.

In an embodiment, a method for producing adipates with waste stream products includes obtaining carbon dioxide from a waste stream of another process, obtaining biomass from a waste stream of another process, pyrolyzing the biomass to produce acetylene, and using the acetylene and the carbon dioxide as reactants for producing adipates.

DETAILED DESCRIPTION

Elementary saturated dicarboxylic acids and corresponding diesters, may generally be represented by the formula —ROOC—$(CH_2)_n$—COOR, where R is —H for the diacids, and R is any alkyl or aryl group for diesters. For diesters, each R may be a same or different alkyl or aryl group. Methods disclosed herein may be used to produce dicarboxylic acids and diesters having (n) intermediate carbon atoms disposed between the two carbons provided by the terminal carbonyl groups, for a total of (n+2) carbons. Some examples of dicarboxylic acids and corresponding diesters are represented in Table 1.

TABLE 1

| | ROOC—$(CH_2)_n$—COOR | | |
|---|---|---|---|
| | Diacids R = H | | Diesters R = alkyl |
| n = | Common Name | IUPAC Name | Common Name |
| 0 | oxalic acid | ethanedioic acid | dialkyl oxalate |
| 1 | malonic acid | propanedioic acid | dialkyl malonate |
| 2 | succinic acid | butanedioic acid | dialkyl succinate |
| 3 | glutaric acid | pentanedioic acid | dialkyl glutarate |
| 4 | adipic acid | hexanedioic acid | dialkyl adipate |
| 5 | pimelic acid | heptanedioic acid | dialkyl pimelate |
| 6 | suberic acid | octanedioic acid | dialkyl suberate |
| 7 | azeleic acid | nonanedioic acid | dialkyl azelate |
| 8 | sebacic acid | decanedioic acid | dialkyl sebacate |
| 18 | | icosanedioic acid | |

The methods disclosed herein are particularly well suited for production of dicarbonyl compounds such as dicarboxylic acids and diesters where n≥2. Dicarbonyl compounds (dicarboxylic acids and diesters) of formula ROOC—$(CH_2)_n$—COOR, where n≥2, R is —H for the diacids, and R is any alkyl or aryl group for diesters, may be produced from alkynes, which are unsaturated hydrocarbons having at least one triple bond between two adjacent carbon atoms (—C≡C—). The simplest alkyne with n=2 is acetylene H—C≡C—H.

Dicarbonyl compounds of formula ROOC—$(CH_2)_n$—COOR, where n≥2 may be produced by hydrogenating bis-carbonyl alkynes of formula ROOC—$(C_nH_{(2n-4m)})$—COOR, where m is a number of (—C≡C—) and $n/2 \geq m \geq 1$. In an embodiment, n may be less than or equal to about 20. As examples, n may be 2, 3, 4, 5, 6, 7, 8, 9, 10, 11, 12, 13, 14, 15, 16, 17, 18, 19 or 20. In an embodiment, the hydrogenating may include catalytic hydrogenation.

Figure 1:
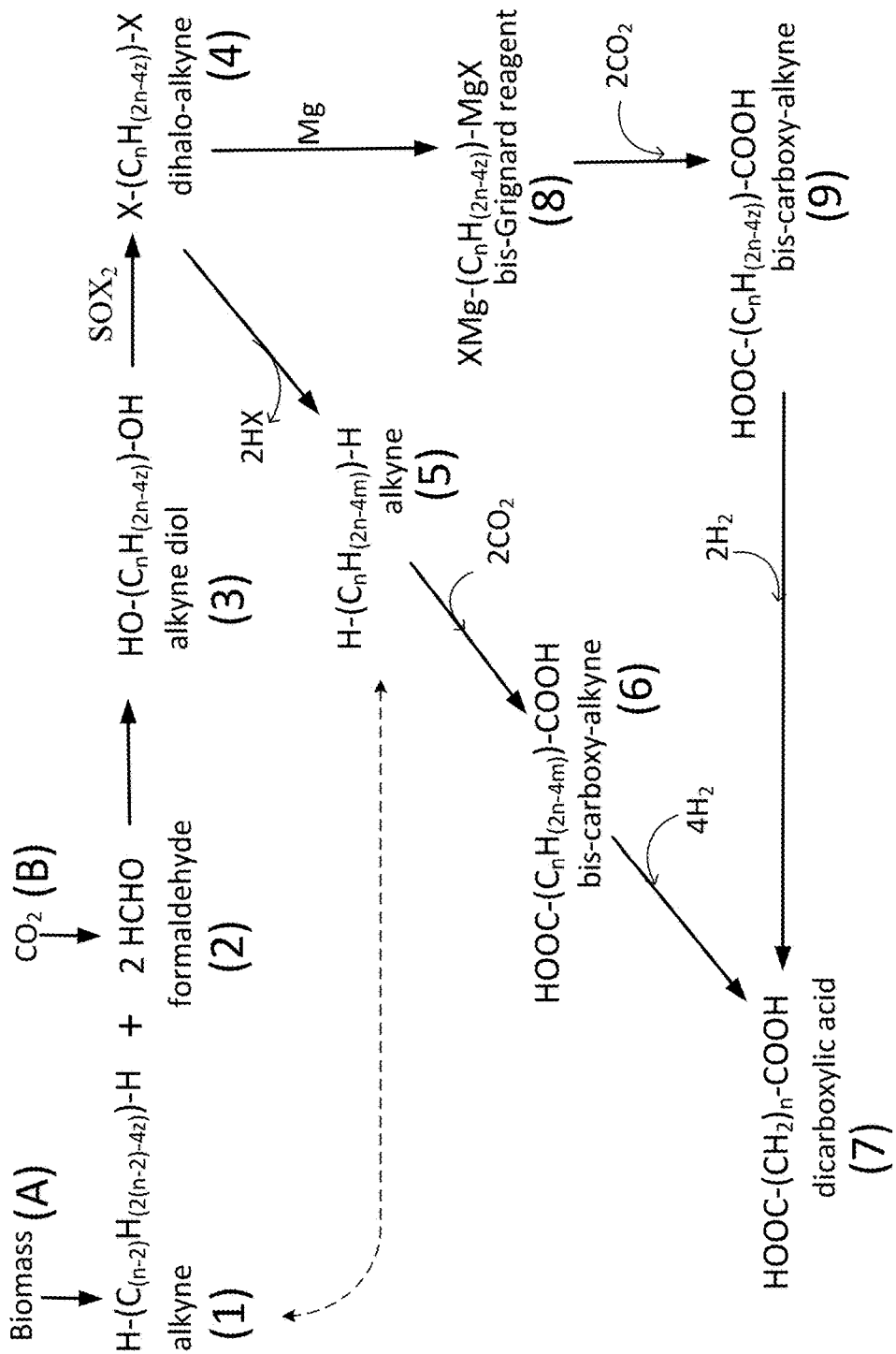
FIG. 1 depicts a general reaction scheme for producing dicarboxylic acids from alkynes according to some embodiments.
Figure 2:
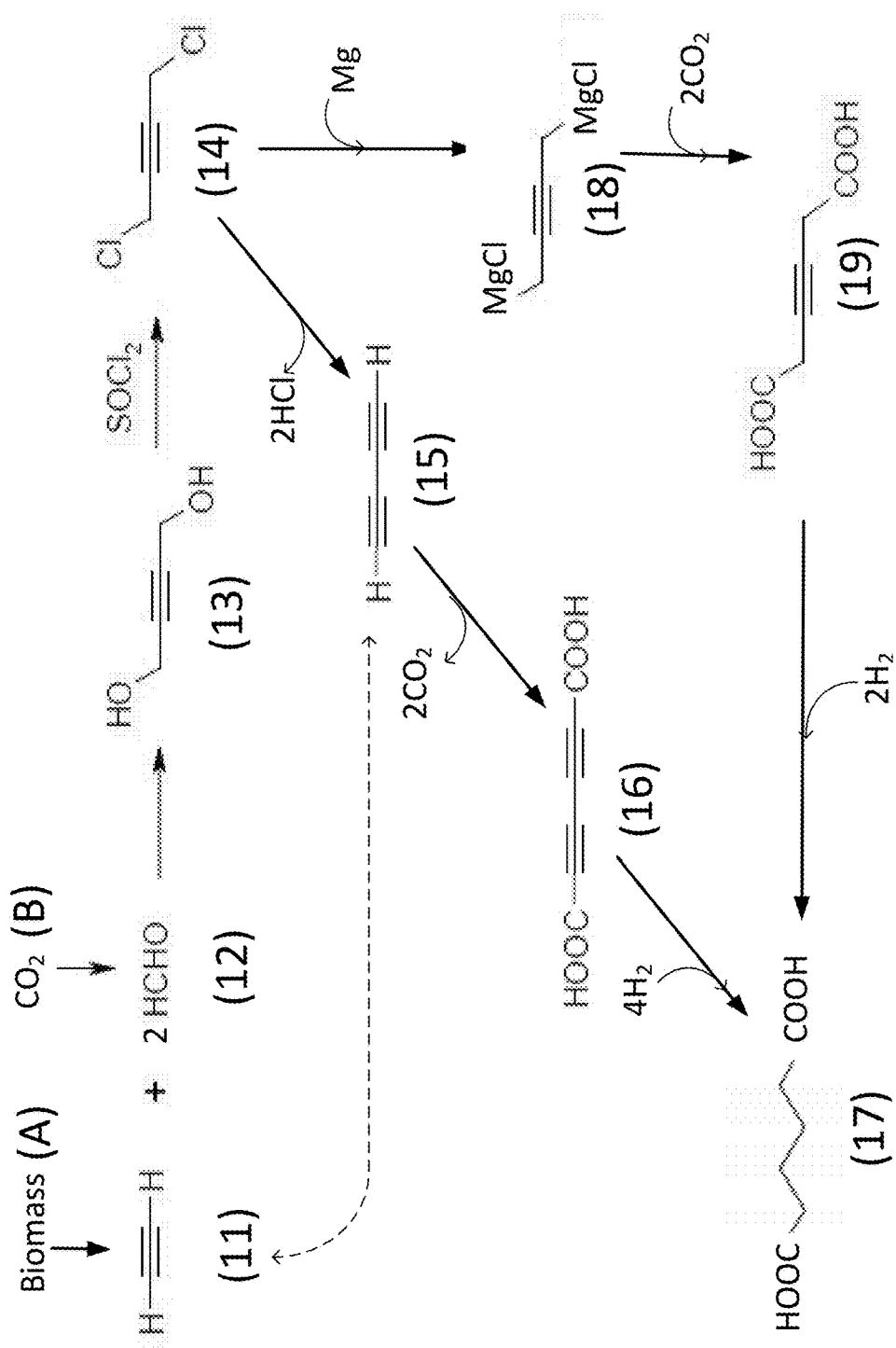
FIG. 2 depicts reaction steps for producing adipic acid from waste stream products according to embodiments.

In an embodiment for producing diacids as shown in FIG. 1, dicarboxylic acids 7 may be produced by hydrogenating bis-carboxy-alkynes 6 or 9. More specifically, in an embodiment as shown in FIG. 2, adipic acid 17 may be produced by hydrogenating dicarboxydiacetylene 16 or bis-carboxy-butyne 19. (For nomenclature purposes, in chemistry, the prefix bis- may sometimes be used instead of the prefix di-. For example, bis-carboxy alkyne refers to an alkyne with 2 carboxy groups.) Some examples of bis-carbonyl alkynes and dicarboxylic acids that may be produced therefrom are represented in Table 2.

TABLE 2

| n = | m = | 2n − 4m = | bis-carbonyl alkyne ROOC—($C_nH_{(2n-4m)}$)—COOR | diester R = alkyl, aryl dicarboxylic acid R = H ROOC—$(CH_2)_n$—COOR |
|---|---|---|---|---|
| 2 | 1 | 0 | ROOC—C≡C—COOR | ROOC—$(CH_2)_2$—COOR |
| 3 | 1 | 2 | ROOC—C≡C—$CH_2$—COOR | ROOC—$(CH_2)_3$—COOR |
| 4 | 1 | 4 | ROOC—C≡C—$CH_2$—$CH_2$—COOR | ROOC—$(CH_2)_4$—COOR |
| 4 | 2 | 0 | ROOC—C≡C—C≡C—COOR | ROOC—$(CH_2)_4$—COOR |
| 5 | 1 | 6 | ROOC—C≡C—$CH_2$—$CH_2$—$CH_2$—COOR | ROOC—$(CH_2)_5$—COOR |
| 5 | 2 | 2 | ROOC—C≡C—$CH_2$—C≡C—COOR | ROOC—$(CH_2)_5$—COOR |
| 6 | 3 | 0 | ROOC—C≡C—C≡C—C≡C—COOR | ROOC—$(CH_2)_6$—COOR |

Referring to FIG. 1, the alkynes 6, 9 may be catalytically hydrogenated by contacting the alkynes with hydrogen in the presence of a hydrogenation catalyst to produce the dicarboxylic acids 7. The reaction may be conducted at temperatures of about ambient temperature to about 100° C., and at pressures of about 1 bar to about 100 bar. In an embodiment, the reaction may be done at ambient temperature and pressure. The hydrogenation catalyst may include platinum, palladium, rhodium, ruthenium, nickel, cobalt, iron, molybdenum, iridium, rhenium, gold, or any combination thereof.

While the starting raw materials for producing dicarboxylic acids or diesters may be obtained from petrochemical or other conventional sources, the dicarboxylic acids produced in accordance with methods described herein may be composites of carbon atoms produced from waste stream materials. Referring to FIG. 1, one starting material may include alkynes 1 that may be derived from biomass waste products A, and another starting material may include formaldehyde (HCHO) 2 that may be produced from carbon dioxide ($CO_2$) B collected from waste exhaust streams.

To reduce reliance on petrochemicals for the producing dicarboxylic acids and diesters, raw material alkynes may be produced from biomass A in FIG. 1, which may be waste stream biomass, instead of the typical starting materials of methane or hydrocarbons. Some examples of waste biomass may include industrial waste, such as saw-dust and wood scraps from lumber mills, or pulp waste from production of paper products, and municipal waste, such as garbage, and tree and yard trimmings. In an embodiment, for example, acetylene 11, in FIGS. 2 and 4, may be produced from lignocellulosic biomass by rapid pyrolysis of the biomass. Rapid pyrolysis of dry lignin produces a gas that is about 14% acetylene by volume.

Carbon dioxide B in FIGS. 1 to 4, and as used in the embodiments described herein, may be obtained from a waste stream of another process, such as, for example, flue gas from combusting fossil fuels to generate electricity, or from incinerating waste. As such, carbon dioxide may be removed or recovered from waste streams so that excessive carbon dioxide does not enter the atmosphere where it may cause environmental concerns. A system for collecting carbon dioxide, such as the LCDesign™ $CO_2$ Capture Systems from HTC Purenergy, Saskatchewan, Canada, may be used to capture carbon dioxide from exhaust gases produced by combusting hydrocarbons for generating electricity.

In some embodiments, the carbon dioxide B may be catalytically reduced to produce formaldehyde 2, 12 in FIGS. 1 and 2, and the formaldehyde as used in the embodiments described herein. The catalytic reduction can be photocatalytic reduction. For example, a glass tube containing a suspension of titanium dioxide photocatalyst in water may be illuminated with a xenon or mercury arc lamp and carbon dioxide may be bubbled into the tube for several hours to yield an aqueous mixture of formaldehyde 2, 12 and methanol. The formaldehyde 2, 12 may then be separated from the methanol.

In some embodiments, for example as shown in FIG. 1, a dicarboxylic acid 7 of formula HOOC—$(CH_2)_n$—COOH, where n≥2, may be produced from alkynes 1 of formula H—($C_{(n-2)}H_{(2(n-2)-4z)}$)—H, where z is the number of original triple bonds (—C≡C). By reacting the alkynes 1 with two equivalents of formaldehyde (HCHO) 2 in the presence of a second metal catalyst, alkyne diols 3 of formula HO—($C_nH_{(2n-4z)}$)—OH may be produced. By using waste biomass to make the alkynes and waste carbon dioxide to make the formaldehyde, all of the carbons of the alkyne diol 3 may be provided, in some embodiments, by waste materials. In an embodiment, the second metal catalyst may be copper, silver, bismuth, or a combination thereof. In an embodiment, as depicted in FIG. 2 for example, butynediol 13 may be produced by a Reppe process that involves treatment of an aqueous mixture of formaldehyde 12 and a copper-bismuth catalyst with acetylene 11 to yield butynediol 13.

In some embodiments, for example as shown in FIG. 1, the alkyne diols 3 of formula HO—($C_nH_{(2n-4z)}$)—OH may be treated with thionyl halides ($SOX_2$) to produce dihalo-alkynes 4 of formula X—($C_nH_{(2n-4z)}$)—X, where X may be any halogen, F, Cl, Br, I, or At. In an embodiment, the treating with thionyl halides may be performed in the presence of a reaction catalyst. Alternative halogenating reagents may include phosphorous trihalides ($PX_3$) or phosphorus pentahalides ($PX_5$). The reaction catalyst may be pyridine, dimethylformamide, or both. In an embodiment, the diols may be cooled with pyridine in an ice bath, and the halogenating regent may be slowly added. The alkynes may be isolated by solvent extraction from the reaction mixture.

As shown in FIG. 1, dihalo-alkynes 4 may be converted to dicarboxylic acids 7 by at least two different reaction sequences. In a first sequence, the dihalo-alkynes 4 of formula X—($C_nH_{(2n-4z)}$)—X may be converted to alkynes 5 of formula H—($C_nH_{(2n-4m)}$)—H, where m is the number of triple bonds (—C≡C—) and m=z+1. This conversion may be carried out by a base promoted elimination of hydrogen halide from the dihalo-alkynes 4. In an embodiment, the dihalo-alkynes may be added slowly to a mixture of aqueous potassium hydroxide and dimethyl sulfoxide while bubbling an inert gas through the solution. The produced gases may be conducted into a solvent, such as tetrahydrofuran to capture the alkynes.

At this juncture, as represented by the dashed line in FIG. 1, if longer alkynes are desired, the above reaction sequence may be repeated with a substitution of the alkynes 5 into the sequence for alkynes 1. Alternatively, bis-carboxy alkynes 6 of formula HOOC—$(C_nH_{(2n-4m)})$—COOH may be produced by carboxylation of the alkynes 5 of formula H—$(C_nH_{(2n-4m)})$—H with two equivalents of carbon dioxide. The carboxylation may be performed with or without the presence of a first metal catalyst. The first metal catalyst may be copper, silver, bismuth, or any combination thereof. In an embodiment, the carboxylation may be conducted by bubbling carbon dioxide gas through ice cold mixture of a dianion of the alkyne with lithium or magnesium as a counter ion. The carbon dioxide, as mentioned above, may be obtained from a waste stream of another process, thereby adding two additional waste stream carbons to the alkynes. As discussed previously, the bis-carboxy alkynes 6 may be catalytically hydrogenated by contacting the alkynes with hydrogen in the presence of a hydrogenation catalyst to produce the dicarboxylic acids 7.

In another embodiment, a second sequence in FIG. 1 for converting the dihalo-alkynes 4 to the dicarboxylic acids 7 may be through an intermediate organometallic compound, such as a Grignard reagent 8. The dihalo-alkynes 4 of formula X—$(C_nH_{(2n-4z)})$—X may be converted to a corresponding bis-Grignard reagent 8 of formula XMg—$(C_nH_{(2n-4z)})$—MgX by treating the dihalo-alkynes with magnesium metal, wherein each X may be the same or different one of F, Cl, Br, I and At. The bis-Grignard reagent may subsequently be treated with excess carbon dioxide to yield bis-carboxy-alkynes 9 of formula HOOC—$(C_nH_{(2n-4z)})$—COOH. The $CO_2$ for this reaction may also be obtained from a waste stream of another process, thereby adding two additional waste stream carbons to the alkyne. As discussed previously, the bis-carboxy alkynes 9 may be catalytically hydrogenated by contacting the alkynes with hydrogen in the presence of a hydrogenation catalyst to produce the dicarboxylic acids 7.

The reaction sequence as described above may be followed as described for producing dicarboxylic acids 7 from biomass A and carbon dioxide B, or if other materials mentioned are available as raw materials, or produced to be raw materials via other processes, the sequence described may be picked up at the appropriate point in the sequence. For example, if alkynes 5 of an appropriate carbon length are available, the alkynes 5 could be the starting material, and would be carboxylated to produce bis-carboxy-alkynes 6, that subsequently would be hydrogenated to produce the desired dicarboxylic acid 7. Thus, the methods may be practiced with waste streams as source of reactants, or with commercially available reactants, or a combination thereof.

In the embodiments as shown in FIG. 2, adipic acid 17 may be produced from acetylene 11 and formaldehyde 12, which may be produced respectively from biomass A and carbon dioxide B. Thus, adipic acid may be produced from the waste stream carbon dioxide and waste biomass, where four of the six carbon atoms of adipic acid may be provided from carbon dioxide and the other two carbon atoms from biomass derived acetylene. In general, a process for producing adipic acid 17 may therefore include obtaining biomass A from a waste stream, obtaining carbon dioxide B from a waste stream, pyrolyzing the biomass to produce acetylene 11, and using the acetylene and the carbon dioxide as reactants for producing adipic acid.

In some embodiments, for example as shown in FIG. 2, the carbon dioxide B may be reduced to formaldehyde 12 so that each formaldehyde carbon may be provided by a carbon of waste carbon dioxide. In a subsequent reaction step, 2-butyne-1,4-diol 13 may be produced by contacting acetylene 11 and formaldehyde 12 in the presence of a second metal catalyst as described herein. As such, the 2-butyne-1,4-diol 13 may have all four carbons provided by waste material, two from the acetylene, and one from each of two molecules of formaldehyde.

The 2-butyne-1,4-diol may be treated with a thionyl halide such as thionyl chloride ($SOCl_2$) to produce dichlorobutyne 14 (1,4-dichloro-2-butyne), retaining the four waste material carbons. The dichlorobutyne 14 may then subsequently be converted to adipic acid 17 by either hydrogen elimination route or the Grignard reagent route described above.

By following the first sequence, diacetylene 15 may be produced by base promoted elimination of HCl from the dichlorobutyne 14. The diacetylene 15 may then be carboxylated in the presence of a first metal catalyst to produce dicarboxydiacetylene 16, adding two additional carbons and increasing the number of carbons to six. The first metal catalyst may include copper, silver, bismuth, or combinations thereof. If the carboxylation is done with waste stream carbon dioxide the additional two carbons may also be waste stream carbons, so that four of the six carbons are from waste carbon dioxide and the other two carbons from waste biomass. The dicarboxydiacetylene 16 may then be hydrogenated to produce adipic acid 17, retaining the six waste stream carbons.

Alternatively, by following the second sequence, a dihalo-alkyne such as dichlorobutyne 14 may be converted to the corresponding bis-Grignard reagent 18 of formula XMg—$(C_nH_{(2n-4z)})$—MgX by treating the dihalo-alkyne (dichlorobutyne 14 in FIG. 2) with magnesium metal, wherein each X may be the same or different one of F, Cl, Br, I and At. The Grignard reagent 18 may then be carboxylated to yield bis-carboxy-butyne 19, which may then be hydrogenated to produce adipic acid 17. As above, the carboxylation may be performed with waste stream carbon dioxide so that all of the carbons in the adipic acid may be waste stream carbons.

Figures 3, 4:
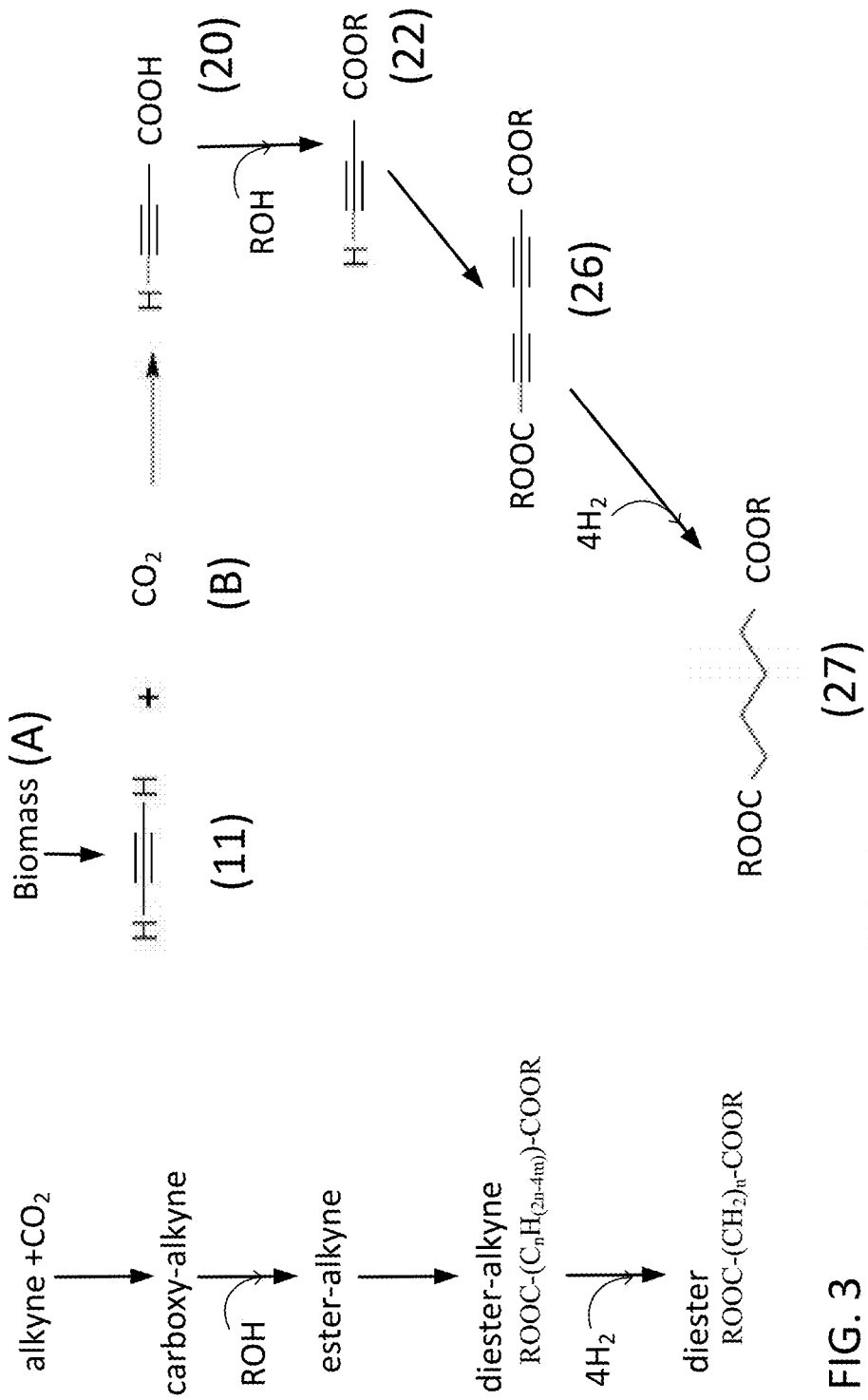
FIG. 3 depicts reaction steps for producing a dialkyl ester from waste stream products according to embodiments.
FIG. 4 depicts reaction steps for producing a dialkyl adipate from waste stream products according to embodiments.

In an embodiment for producing diesters, as generally represented in FIG. 3, diesters of formula ROOC—$(CH_2)_n$—COOR may be produced by hydrogenating diester-alkynes of formula ROOC—$(C_nH_{(2n-4m)})$—COOR. The diester-alkynes may be produced from carbon dioxide and alkynes that, as discussed above, may be from waste stream processes. Carboxylation of an alkyne with carbon dioxide may produce mono-carboxyl-alkynes having only one terminal carboxyl group leaving the other terminal end available for dimerization. Mono-ester alkynes may be prepared from the mono-carboxyl-alkynes by esterification of the carboxyl groups. Mono-ester alkynes may be dimerized to produce the diester alkynes. The dimerization can, for example, be Glaser-Hay dimerization.

More specifically, in an embodiment as shown in FIG. 4, the diester, dialkyl adipate 27, may be produced by hydrogenating dialkyl diacetylene dicarboxylate 26. In an embodiment, each R may be the same or a different one of any alkyl or aryl group. In embodiments, R may be C1-C5 alkyl, or substituted alkyl. In embodiments, R may be methyl, ethyl, propyl, butyl, or pentyl. In the representation of FIG. 4, R may also be —H and the adipate product would then be the diacid adipic acid.

As discussed above, waste biomass A may be converted to acetylene 11. Mono anions of acetylene 11 may be reacted with carbon dioxide B that may be from a waste stream of another process, to produce propiolic acid 20. Similarly, alkynes of various other carbon-chain lengths may be carboxylated to produce mono-carboxy-alkynes of the corresponding carbon-chain length. The carboxylic acid 20 may be converted to an ester, which as depicted in the embodiment of FIG. 4 may be methyl propiolate 22, by an esterification process with an alkanol (alkyl alcohol), wherein methyl alcohol may provide methyl propiolate, for example. A catalyzed dimerization of the esterified terminal alkynes 22 may be used to produce diester-alkynes 26, which as depicted in the embodiment of FIG. 4 may be dialkyl diacetylene dicarboxylate. Hydrogenation of the diester-alkynes 26 may then produce diesters 27, which as depicted in the embodiment of FIG. 4 may be dialkyl adipate.

EXAMPLES

Example 1: A Method for Producing Adipic Acid

Adipic acid (HOOC—$(CH_2)_4$—COOH) 17 is produced by hydrogenating dicarboxydiacetylene (HOOC—C≡C—C≡C—COOH) 16 in the presence of platinum as a catalyst. A mixture of the di-lithium salt of dicarboxydiacetylene (1 equivalent), 10% platinum on activated carbon (0.05 equivalent platinum), and 1 M phosphate buffer (pH 7.4) in an autoclave is treated with hydrogen gas (about 35 atmospheres) for about 3 hours. The catalyst is removed by filtration and the filtrate is acidified by addition of concentrated hydrochloric acid. After cooling in an ice bath the solid is filtered and dried under reduced pressure to yield adipic acid.

Example 2: Production of 1,4-dichloro-2-butyne

Adipic acid 17 is produced from acetylene A, derived from waste stream biomass materials, and waste stream carbon dioxide B. A system for collecting carbon dioxide B, such as the LCDesign™ $CO_2$ Capture Systems from HTC Purenergy, Saskatchewan, Canada, is used to capture $CO_2$ from exhaust gases produced by combusting hydrocarbons for generating electricity. The carbon dioxide B is photocatalytically reduced to formaldehyde 12 by providing a glass tube containing a suspension of titanium dioxide photocatalyst in water and illuminated with a xenon or mercury arc lamp, and bubbling carbon dioxide into the tube for several hours to yield an aqueous mixture of formaldehyde and methanol, and separating the formaldehyde from the methanol.

2-Butyne-1,4-diol is synthesized from acetylene 11 and formaldehyde 12 in the presence of a catalyst. Into a mixture of 45% aqueous formaldehyde (1 equivalent) and malachite crystal-based copper-acetylide complex catalyst (0.0017 equivalent) is bubbled acetylene at a pressure of about 5 psig while heating at about 90° C. and maintaining the pH at about 6 with saturated sodium bicarbonate solution for about 2 hours. After removal of the catalyst by filtration, fractional distillation under reduced pressure yields 2-butyne-1,4-diol 13.

The 2-butyne-1,4-diol 13 is then halogenated. A mixture of butynediol (1 equivalent) and pyridine (0.1 equivalent) is cooled in an ice-salt bath, and ice cold thionyl chloride (2 equivalents) is slowly added. After about 1 hour the ice-salt bath is replaced with an ice-water bath, and the mixture is stirred for about 20 hours, after which ice-water is added and the mixture is extracted with diethyl ether. The extract is dried over magnesium sulfate and concentrated under reduced pressure. The residue is purified by reduced pressure distillation to yield 1,4-dichloro-2-butyne 14.

Example 3: Production of Adipic Acid via Diacetylene

The 1,4-dichloro-2-butyne 14 of Example 2 is de-halogenated by base promoted elimination of HCl to produce diacetylene 15. A mixture of 4 M aqueous potassium hydroxide (3 equivalents) and dimethyl sulfoxide (1 mL per 16 mmol potassium hydroxide) is heated to about 70-75° C. 1,4-dichloro-2-butyne (1 equivalent) is added slowly to the mixture while bubbling argon through the solution. The volatile product is directed through a series of two gas washing bottles containing dilute aqueous potassium hydroxide followed by two calcium chloride drying tubes and into a vessel containing anhydrous tetrahydrofuran cooled in an ice-calcium chloride bath to yield a tetrahydrofuran solution of diacetylene 15.

The solution of diacetylene (1 equivalent) in tetrahydrofuran is cooled in an ice-calcium chloride bath, and a 1.6 M solution of n-butyl lithium (2 equivalents) in hexane is slowly added. Into this mixture is bubbled dry carbon dioxide. The cooling bath is replaced with an ice-water bath and bubbling with carbon dioxide is continued for about 1 hour. The reaction is quenched by treatment with a minimum volume of water. Removal of solvents under reduced pressure yields the di-lithium salt of diacetylene dicarboxylic acid.

Adipic acid 17 is then produced from the dicarboxydiacetylene 16 by hydrogenating the dicarboxydiacetylene in the presence of palladium as a catalyst according to the method described in Example 1.

Example 4: Production of Dimethyl Adipate

Dimethyl adipate 27 may be derived from waste stream biomass materials A, and waste stream carbon dioxide B. Biomass material A is converted to acetylene 11, and the acetylene is reacted with $CO_2$ B to produce propiolic acid 20. Via an esterification of the propiolic acid 20 with methanol, the propiolic acid is converted to methyl propiolate (in FIG. 4, structure 22 with R=$CH_3$).

A Glaser-Hay dimerization involving copper catalyzed dimerization of terminal alkynes is used to convert the methyl propiolate 22 to dimethyl diacetylene dicarboxylate (in FIG. 4, structure 26 with R=$CH_3$). A mixture of copper (II) chloride (0.1 equivalent), tetramethylethylenediamine (0.03 equivalent) and acetone as solvent is stirred for 40 minutes. To this mixture is added a solution of methyl propiolate (1 equivalent) in acetone. After bubbling oxygen through the mixture for 2 hours, the solvent is removed under reduced pressure, and the residue is treated with diethyl ether. The organic phase is washed with 5% hydrochloric acid, dried over magnesium sulfate, and concentrated under reduced pressure to yield dimethyl diacetylene dicarboxylate 26.

For hydrogenation of the alkyne, a mixture of dimethyl diacetylene dicarboxylate (1 equivalent), 10% palladium on carbon (0.02 equivalent palladium) and ethyl acetate as solvent is treated with hydrogen gas (3 atmospheres). After about 5 hours, the catalyst is removed by filtration, and the filtrate is concentrated under reduced pressure to yield dimethyl adipate.

Therefore, the examples demonstrate that dicarboxylic acids, such as adipic acid, and diesters, such as adipates, can be produced from waste materials derived from biomass and/or collected from waste stream processes that generate waste carbon dioxide, thereby reducing the need for petrochemically derived raw materials.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc.

As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for producing dicarbonyl compound of formula I:

$$ROOC-(CH_2)_n-COOR \qquad (I),$$

wherein R is —H and n=4, the method comprising:
hydrogenating a bis-carbonyl alkyne of formula II:

$$ROOC-(C_nH_{(2n-4m)})-COOR \qquad (II),$$

wherein R is —H, n=4, and m=2, wherein hydrogenating comprises reacting the bis-carbonyl alkyne of formula II with hydrogen gas in the presence of catalyst selected from the group consisting of platinum and palladium, for about 3 h.

2. The method of claim 1, further comprising carboxylating an alkyne of formula III:

$$H-(C_nH_{(2n-4m)})-H \qquad (III),$$

wherein n=4, m=2, with two equivalents of $CO_2$ in the presence of a first metal catalyst to produce the bis-carbonyl alkyne of formula II, wherein the first metal catalyst comprises copper, silver, bismuth, or combinations thereof.

3. The method of claim 2, further comprising preparing the alkyne of formula III by base promoted elimination of hydrogen halide from a dihalo-alkyne of formula IV:

$$X-(C_nH_{(2n-4z)})-X \qquad (IV),$$

wherein n=4, z=2,
and
each X comprises a same or different one of F, Cl, Br, I, and At.

4. The method of claim 3, wherein preparing the dihalo-alkyne of formula IV comprises treating an alkyne diol of formula V:

$$HO-(C_nH_{(2n-4z)})-OH \qquad (V)$$

wherein n=4, z=2, with thionyl halides of formula $SOX_2$, wherein each X comprises a same or different one of F, Cl, Br, I, and At.

5. The method of claim 4, further comprises preparing the alkyne diol of formula V by reacting an alkyne of formula VI:

$$H-(C_{(n-2)}H_{(2(n-2)-4z)})-H \qquad (VI)$$

wherein n=4, z=1, with 2 equivalents of formaldehyde in the presence of a second metal catalyst comprising copper, silver, bismuth, or combinations thereof.

6. The method of claim 1, further comprising producing the bis-carboxy alkyne of formula II: $ROOC-(C_nH_{(2n-4m)})-COOR$ (II), wherein R is —H, n=4, and m=2 by carboxylating diacetylene with $CO_2$ in the presence of a first metal catalyst including copper, silver, bismuth, or combinations thereof.

7. The method of claim 6, further comprising producing the diacetylene by base promoted elimination of HCl from 1,4-dihalo-2-butyne.

8. The method of claim 7, further comprising producing the 1,4-dihalo-2-butyne by treating 2-butyne-1,4-diol with thionyl chloride.

9. The method of claim 8, further comprising producing the 2-butyne-1,4-diol by contacting acetylene and formaldehyde in the presence of a second metal catalyst including copper, silver, bismuth, or combinations thereof.

10. The method of claim 9, further comprising producing the acetylene by pyrolysis of lignocellulosic biomass.

* * * * *